(12) United States Patent
Voevodin

(10) Patent No.: US 6,320,190 B1
(45) Date of Patent: Nov. 20, 2001

(54) AIR SHIELD FOR A PARTICLE DETECTION SYSTEM

(76) Inventor: Trevor Richard Voevodin, 581 Old Cleveland Road, Camp Hill, Queensland, 4152 (AU)

( * ) Notice: Subject to any disclaimer, the term of this patent is extended or adjusted under 35 U.S.C. 154(b) by 0 days.

(21) Appl. No.: 09/312,226

(22) Filed: May 14, 1999

(30) Foreign Application Priority Data

May 15, 1998 (AU) .................................................. PP 3520

(51) Int. Cl.⁷ .................................................. G01N 21/00
(52) U.S. Cl. .................................. 250/338.5; 250/338.1; 250/339.07; 250/324; 250/559.4
(58) Field of Search ........................... 250/338.5, 338.1, 250/339.07, 324, 559.4

(56) References Cited

U.S. PATENT DOCUMENTS

| 4,340,326 | * | 7/1982 | Buonauro et al. | ................. 250/559.4 |
| 5,493,117 | * | 2/1996 | Tamaki et al. | ....................... 250/324 |
| 5,517,314 | * | 5/1996 | Wallin | ............................... 250/338.5 |

* cited by examiner

Primary Examiner—Constantine Hannaher
Assistant Examiner—Andrew Israel
(74) Attorney, Agent, or Firm—William H. Eilberg

(57) ABSTRACT

A shield for a detector or prism of a particle detection system has a body mountable on the detector or prism, divided into first and second compartments by an intermediate wall with a hole therethrough. Air diffuser units In the first compartment (adjacent the detector or prism) generate a stable column of air which prevents the particles contacting the beam window of the detector or prism.

**30 Claims,

AIR SHIELD FOR A PARTICLE DETECTION SYSTEM

BACKGROUND OF THE INVENTION

1. Field of the Invention

THIS INVENTION relates to an air shield for a particle detection system.

The invention is particularly suitable for, but not limited to, an air shield for a smoke detection system.

2. Prior Art

FIG. 1 discloses the operating principle of a known smoke detection system

The transmitter (101) in the detector (100) emits an invisible Infra-red (IR) pulse through the transmitter lens. The IR pulse traverses the measuring section and reaches the reflector (102) (eg., a prism) located opposite the detector (100). The reflector deflects the IR pulse back to the detector (100) where a receiver lens (103) directs the reflected IR pulse to a silicon photodiode (104). The resulting electrical signal is evaluated by the electronics.

If smoke (110) penetrates the measuring section, part of the IR pulse is absorbed by the smoke particles, while another part is scattered by the smoke particles. The remaining light reaches the reflector (102) and is then reflected and once again passes through the measuring section and is further attenuated. As only a small portion of the beam reaches the receiver (103), the signal becomes smaller.

The detection system disclosed in FIG. 1 has the advantage over earlier systems, which had a transmitter at one end of the measuring section and a receiver at the other end of the measuring section, that a power supply and monitoring electronics need only be connected to the detector (100) at one end of the system. This is a significant saving where the measuring section, eg., in a large warehouse, may extend over 200 meters.

The problem with both known systems is that dust, smoke or other particles can cover the "windows" of the detectors and reflectors, degrading the performance of the detection systems and, in extreme cases, causing failure.

One suggestion has been to blow or direct a curtain of air across the beam windows, but this has proved unsuccessful as it has been found that the curtain of air actually draws dust or other particles from the surrounding air into the curtain, and these particles are deposited on the beam windows, merely delaying the period in which the build-up of dust or other particles on the beam windows becomes unacceptable.

SUMMARY OF THE PRESENT INVENTION

It is an object of the present invention to provide an air shield for a particle detection system component where a column of air is generated to prevent (or at least minimise) the contact of particles with the beam windows.

It is a preferred object of the present invention to provide an air shield where the air can be provided by the reticulated air supply found in most buildings.

It is a further preferred object to provide an air shield which is relatively inexpensive to manufacture, easy to install and requires minimal, if any, maintenance.

Other preferred objects of the present invention will become apparent from the following description.

In one aspect, the present invention resides in a method for shielding a component of a particle detection system from the particles, including the steps of:

mounting an air shield on the component, the air shield having a tubular body divided into first and second compartments by an intermediate wall, having a hole therethrough, the end of the body adjacent the first compartment being engageable with the component; and applying pressurised air to the first compartment to pass through the hole and into the second component in a substantially stable column flow to prevent the ingress of particles into the tubular body.

In a second aspect, the present invention resides in an air shield for a component of a particle detection system including:

a tubular body, open at both ends, divided into first and second compartments by an Intermediate wall having a hole therethrough, the end of the body adjacent the first compartment being engageable with (or mountable on) the component; and air diffuser means In the first compartment, connectable to a source of pressurised air; so arranged that:

a column of substantially stable air flows from the first compartment through the hole in the Intermediate wall, and through the second compartment and is expelled from the other end of the body to protect the component from the particles.

The shield is preferably formed from transparent plastics material, eg., perspex or polycarbonate, or from stainless steel. The body may be square, rectangular, circular, or other shape in end view and is preferably formed for releasable mounting on the component which it is designed to protect.

Preferably, the intermediate wall is spaced a distance of not less than 50 mm, more preferably 80 mm, from the other end of the tubular body in the second compartment. Preferably, the intermediate wall is spaced not less than 50 mm, more preferably at least 60 mm, from the beam window.

Preferably, at least one air diffuser unit is provided in the first compartment. More preferably, a plurality of the air diffuser units are arranged at substantially equal spacings within the first compartment.

Preferably, each air diffuser unit is of the type where air is diffused through a porous body to minimise any eddies or vortices within the first compartment.

Preferably, the air diffuser units are connected to a manifold which, in turn, is connected to a reticulated air supply (or a compressor).

Preferably, a filter/dryer unit is provided between the air supply source and the air diffuser units.

Preferably, the shape of the hole in the intermediate wall substantially conforms to the shape of the beam window on the component to which the air shield is to be mounted. Preferably, the hole is at least slightly larger than the beam window.

The air shield may be sealed to the component by a silicone sealant or other suitable sealing material.

Preferably, the placement of the air diffuser units, and the volume of air transmitted by the units, generates a stable column of air which passes through the hole in the intermediate wall and the second compartment to be expelled from the tubular body so as to prevent the ingress of any particles, eg., smoke or dust, into the air shield, and thereby preclude contact between the particles and the beam windows.

BRIEF DESCRIPTION OF THE DRAWINGS

To enable the invention to be fully understood, preferred embodiments will now be described with reference to the accompanying drawings in which.

DETAILED DESCRIPTION OF THE PREFERRED EMBODIMENTS

Figure 1:
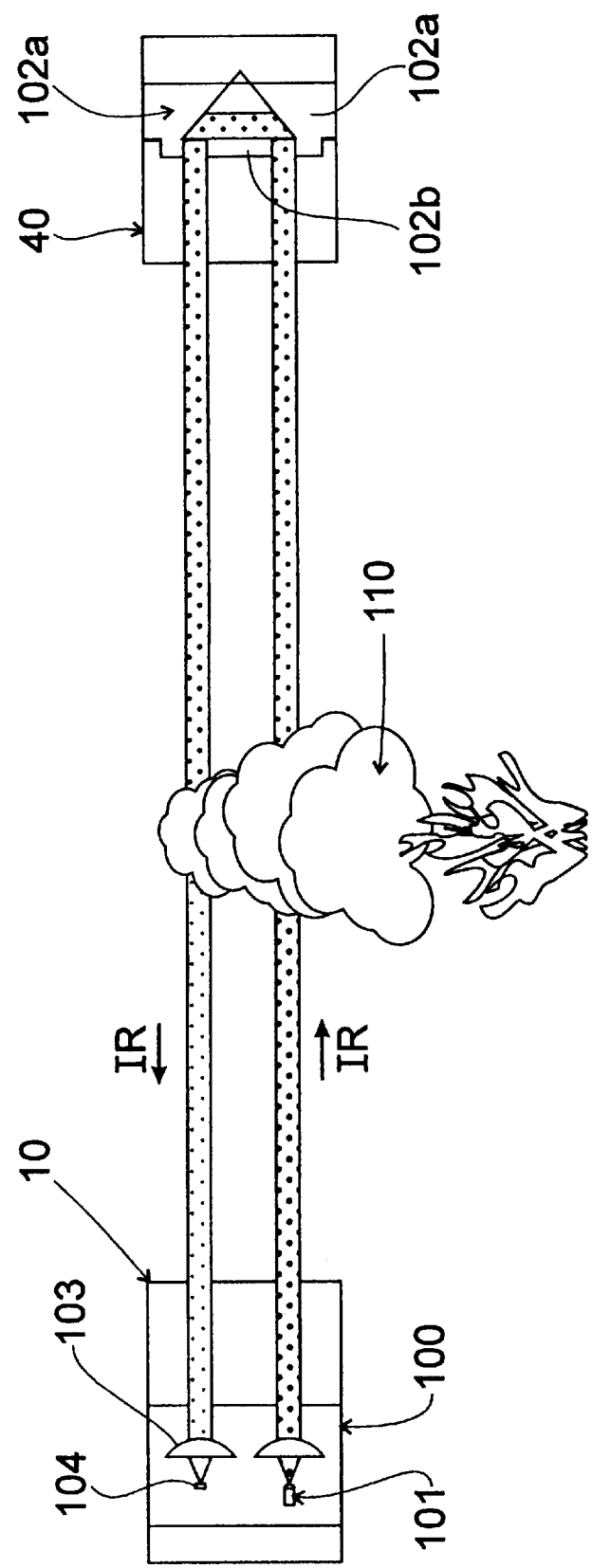
FIG. 1 is a schematic drawing of a known smoke detection system to which the invention may be fitted.
Figure 2:
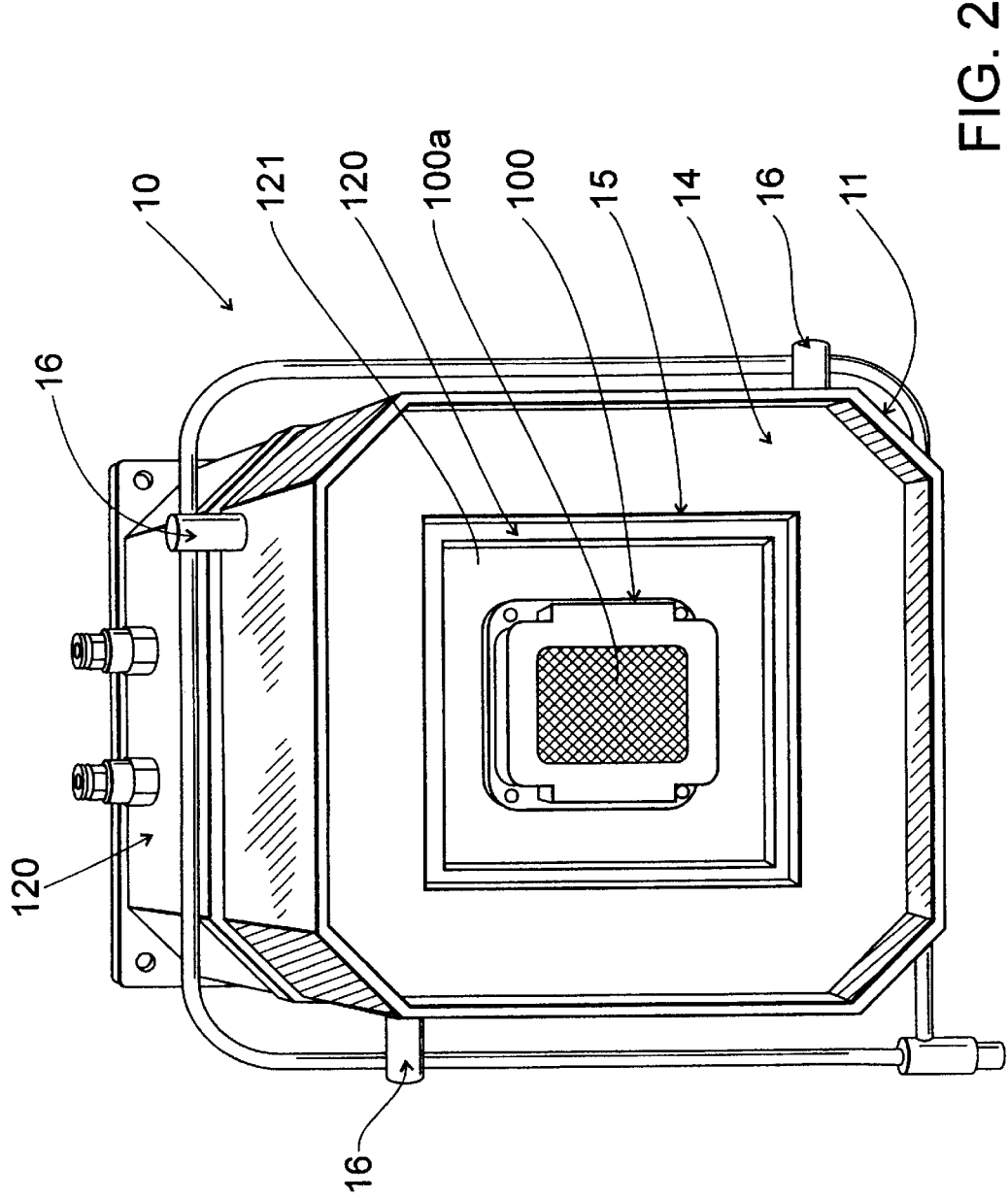
FIG. 2 is a front view of a first embodiment.

The detector 100 (see FIG. 2) and prism 102 (see FIGS. 3 and 4) are mounted in the area to be measured as shown In FIG. 1, eg., a grain or sugar storage facility.

The air shield unit 10 for the detector 100 has a tubular body 11 (see FIG. 2) which is substantially square in end view and is divided into first and second compartments by an intermediate wall 14 having a hole 15 therethrough. The hole 15 is just larger than the window 121 (of a metal housing 120) which protects the beam window 100a on the detector 100. The tubular body is open at both ends and the end adjacent the first compartment is adapted to engage the housing 120 for the detector 100 and may be sealed thereto by silicon sealant (not shown). Preferably, the intermediate wall 14 is spaced at least 60 mm from the window 121.

The tubular body 11 (and internal wall 14) are formed of stainless steel, which is impervious to attack by methyl bromide, which is used to protect the stored material.

Figure 4:
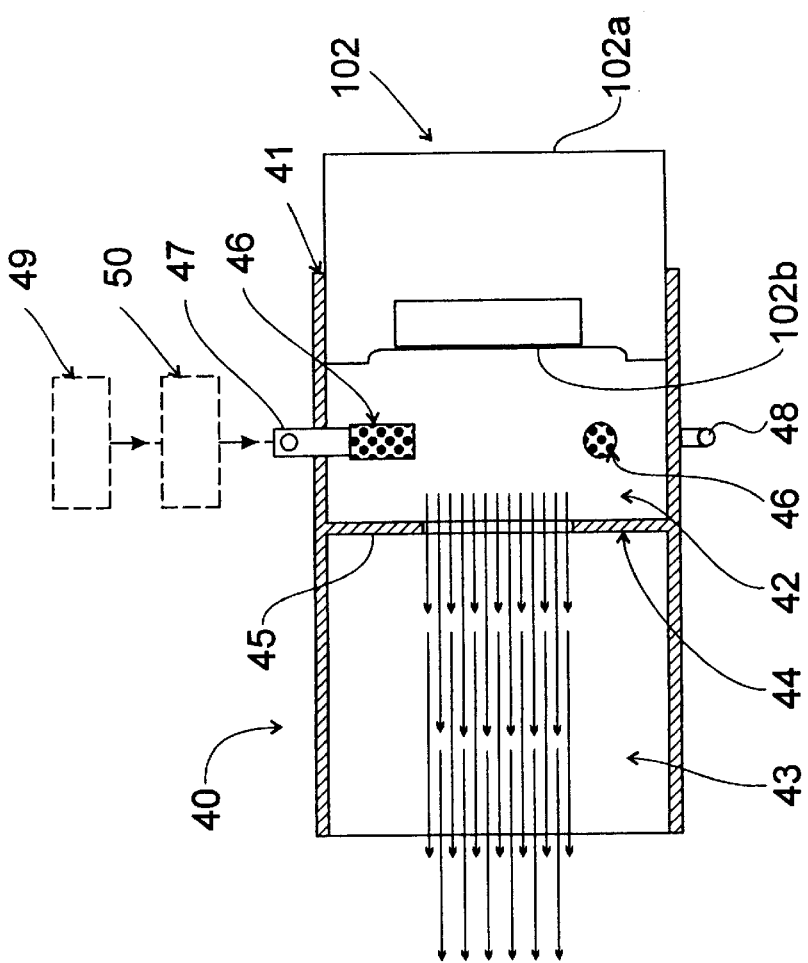
FIGS. 3 and 4 are respective front and sectional side views of a second embodiment.
Figure 3:
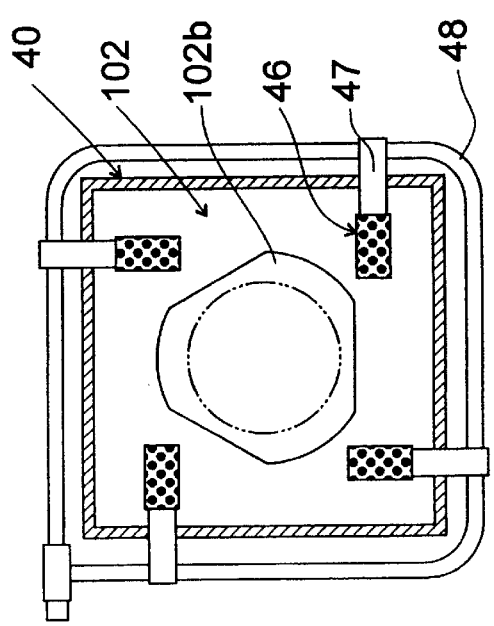

Four air diffuser units 16 are mounted in the first compartment in the manner to be hereinafter described with reference to the embodiment of FIGS. 3 and 4.

The air shield 40, for the prism (see FIGS. 3 and 4) has a tubular body 41 of perspex or polycarbonate and the end adjacent the first compartment 42 is mounted (and sealed) to the body 102a of the prism 102.

The air shield 40 is divided into the first and second compartments 42, 43 by the intermediate wall 44 and the hole 45 is just larger than the beam window 102b for the prism 102.

Four air diffuser units 46 are mounted in the first compartment 42 between the beam window 102b of the prism 102 and the intermediate wall 44. As shown in FIG. 3, the air diffuser units 46 are regularly spaced within the first compartment 42 and do not block the beam window 102b.

Each air diffuser 46 is of the type where air is transmitted through a porous body to minimise the generation of any eddies or vortices within the first compartment 42.

Fittings 47 connect the diffuser units 46 to a manifold 48 which, in turn, is connected to a source of pressurised air 49. The pressurised air may be provided by reticulated a r supply, or via a generator, and preferably, a filter/dryer unit 50 is provided upstream of the manifold 48.

Preferably, the intermediate wall 44 is spaced a distance of not less than 50 mm, more preferably, 80 mm from the open end of the tubular body 41 in the second compartment 43—this assists the column of air becoming stabilized before it exits the shield.

The body 41 of the shield 40 is formed from perspex, polycarbonate or other suitable plastics material. These materials can be used where the detection system is not within a hostile environment Generally, glass is not acceptable for the shield body if the materials being stored are foodstuffs.

It will be readily apparent to the skilled addressee that the air shield assemblies 10, 40 can be easily and relatively inexpensively assembled and installed, and require minimal minimal maintenance, particularly when filtered/dried air is supplied to the air diffusion units 16, 46.

The stable columns of air passing from the first compartments 42 through the holes 15, 45 into the second compartments 43, eliminates (or at least minimises) any eddies or vortices which could draw particles into contact with the beam windows 101a, 102b. Indeed, the column flow of air will exclude the ingress of particles into the tubular bodies 11, 41, and so the beam windows 100a, 102b will be protected against any build-up of particles thereon.

The embodiments described are by way of illustrative examples only and various changes and modifications may be made thereto without departing from the present invention.

I claim:

1. An air shield for a component of a particle detection system including:

a tubular body, open at both ends, divided into first and second compartments by an intermediate wall having a hole therethrough, the end of the body adjacent the first compartment being engageable with (or mountable on) the component; and an air diffuser unit in the first compartment, connectable to a source of pressurised air; so arranged that:

a column of substantially stable air flows from the first compartment through the hole in the intermediate wall, and through the second compartment and is expelled from the other end of the body to protect the component from the particles, wherein the placement of the air diffuser unit, and the volume of air transmitted by the air diffuser unit, generates a stable column of air which passes through the hole in the intermediate wall and the second compartment to be expelled from the tubular body so as to prevent the ingress of any smoke or dust particles into the shield, and thereby preclude contact between the particles and a beam window on the component.

2. A shield as claimed in claim 1 wherein:

the intermediate wall is spaced a distance of not less than 50 mm, more preferably 80 mm, from the other end of the tubular body in the second compartment.

3. A shield as claimed in claim 1 wherein:

the intermediate wall is spaced not less than 50 mm, more preferably at least 60 mm, from the component.

4. A shield as claimed in claim 1 wherein:

the shield is formed from transparent plastics material, or stainless steel; and the body is square, rectangular, circular, or other shape in end view, and is formed for releasable mounting on the component to be protected.

5. A shield as claimed in claim 1 wherein:

the intermediate wall is spaced a distance of not less than 50 mm, more preferably 80 mm, from the other end of the tubular body in the second compartment.

6. A shield as claimed in claim 1 wherein:

the intermediate wall is spaced not less than 50 mm, more preferably at least 60 mm, from the component.

7. A shield as claimed in claim 1 wherein:

at least one air diffuser unit is provided in the first compartment.

8. A shield as claimed in claim 7 wherein:

a plurality of the air diffuser units are arranged at substantially equal spacings within the first compartment.

9. A shield as claimed in claim 8 wherein:

each air diffuser unit is of the type where air is diffused through a porous body to minimise any eddies or vortices within the first compartment.

10. A shield as claimed in claim 8 wherein:

the air diffuser units are connected to a manifold which, in turn, is connected to a pressurised air supply source; and a filter/dryer unit is provided between the air supply source and the air diffuser units.

11. A shield according to claim 1 wherein:

the shape of the hole in the intermediate wall substantially conforms to the shape of a beam window on the component to which the air shield is to be mounted.

12. A shield according to claim 11 wherein:

the hole is at least slightly larger than the beam window.

13. An air shield for a component of a particle detection system including:

a tubular body, open at both ends, divided into first and second compartments by an intermediate wall having a hole therethrough, the end of the body adjacent the first compartment being engageable with (or mountable on) the component; and an air diffuser unit in the first compartment, connectable to a source of pressurised air; so arranged that:

a column of substantially stable air flows from the first compartment through the hole in the intermediate wall, and through the second compartment and is expelled from the other end of the body to protect the component from the particles, wherein the intermediate wall is spaced a distance of not less than 50 mm, more preferably 80 mm, from the other end of the tubular body in the second compartment.

14. A shield as claimed in claim 13 wherein:

the shield is formed from transparent plastics material, or stainless steel; and the body is square, rectangular, circular, or other shape in end view, and is formed for releasable mounting on the component to be protected.

15. A shield as claimed in claim 13 wherein:

at least one air diffuser unit is provided in the first compartment.

16. A shield as claimed in claim 15 wherein:

a plurality of the air diffuser units are arranged at substantially equal spacings within the first compartment.

17. A shield as claimed in claim 16 wherein:

each air diffuser unit is of the type where air is diffused through a porous body to minimise any eddies or vortices within the first compartment.

18. A shield as claimed in claim 16 wherein:

the air diffuser units are connected to a manifold which, in turn, is connected to a pressurised air supply source; and a filter/dryer unit is provided between the air supply source and the air diffuser units.

19. A shield according to claim 13 wherein:

the shape of the hole in the intermediate wall substantially conforms to the shape of a beam window on the component to which the air shield is to be mounted.

20. A shield according to claim 19 wherein:

the hole is at least slightly larger than the beam window.

21. A shield as claimed in claim 13 wherein:

the placement of the air diffuser units, and the volume of air transmitted by the units, generates a stable column of air which passes through the hole in the intermediate wall and the second compartment to be expelled from the tubular body so as to prevent the ingress of any smoke or dust particles into the shield, and thereby preclude contact between the particles and a beam window on the component.

22. An air shield for a component of a particle detection system including:

a tubular body, open at both ends, divided into first and second compartments by an intermediate wall having a hole therethrough, the end of the body adjacent the first compartment being engageable with (or mountable on) the component; and an air diffuser unit in the first compartment, connectable to a source of pressurised air; so arranged that:

a column of substantially stable air flows from the first compartment through the hole in the intermediate wall, and through the second compartment and is expelled from the other end of the body to protect the component from the particles, wherein the intermediate wall is spaced not less than 50 mm, more preferably at least 60 mm, from the component.

23. A shield as claimed in claim 22 wherein:

the shield is formed from transparent plastics material, or stainless steel; and the body is square, rectangular, circular, or other shape in end view, and is formed for releasable mounting on the component to be protected.

24. A shield as claimed in claim 22 wherein:

at least one air diffuser unit is provided in the first compartment.

25. A shield as claimed in claim 22 wherein:

a plurality of the air diffuser units are arranged at substantially equal spacings within the first compartment.

26. A shield as claimed in claim 22 wherein:

each air diffuser unit is of the type where air is diffused through a porous body to minimise any eddies or vortices within the first compartment.

27. A shield as claimed in claim 22 wherein:

the air diffuser units are connected to a manifold which, in turn, is connected to a pressurised air supply source; and a filter/dryer unit is provided between the air supply source and the air diffuser units.

28. A shield according to claim 22 wherein:

the shape of the hole in the intermediate wall substantially conforms to the shape of a beam window on the component to which the air shield is to be mounted.

29. A shield according to claim 22 wherein:

the hole is at least slightly larger than the beam window.

30. A shield as claimed in claim 22 wherein:

the placement of the air diffuser units, and the volume of air transmitted by the units, generates a stable column of air which passes through the hole in the intermediate wall and the second compartment to be expelled from the tubular body so as to prevent the ingress of any smoke or dust particles into the shield, and thereby preclude contact between the particles and a beam window on the component.

* * * * *